United States Patent [19]

Ellison et al.

[11] Patent Number: Plant 6,970

[45] Date of Patent: Aug. 1, 1989

[54] ASPARAGUS PLANT—JERSEY GEM

[75] Inventors: J. Howard Ellison, Milltown; John J. Kinelski, Princeton, both of N.J.

[73] Assignee: Rutger Univ., New Brunswick, N.J.

[21] Appl. No.: 159,685

[22] Filed: Feb. 24, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

An Asparagus plant having all male characteristics, particularly productive under conditions found in North Carolina and Oklahoma where it was highest yielding hybrid over long periods of time and among the top ten in yield in two areas in Michigan, having tolerance to rust (*Puccinia asparagi*) and producing good quality spears.

1 Drawing Sheet

This invention relates to Asparagus plants and particularly to varieties which have outstanding characteristics, and is one of the hybrids which has been developed by us through a long period of selection and crossing and re-crossing as is necessary to produce the best hybrids under widely varying conditions.

GENERAL DESCRIPTION OF THE INVENTION

The hybrid Asparagus which is the subject of this disclosure, has been developed particularly to produce good and large quantities of Asparagus, the same having been tested under widely varying conditions. When compared with other varieties both those which we have developed and which are standards in the industry, it is in fact substantially more productive in virtually all of the instances where tests have been conducted by us with respect thereto and by others from which data has been assembled.

The fact that this particular plant is an all male plant, it therefore does not produce any seed and as a result the volunteer Asparagus seedlings which normally accompany Asparagus grown from seed, are not present. The energy which would otherwise go into seed production is stored in the root system where it enhances higher yields.

In order to identify this particular Asparagus plant in commerce, we have chosen to call the same "Jersey Gem" and as such it has been tested under widely varying conditions in North Carolina, in Michigan, and also Oklahoma, which obviously provide for quite different growth possibilities.

As a matter of fact when tested in Oklahoma for example, it was ranked number two in a trial of forty-one other cultivars, the yield data relating thereto being disclosed in a table supplied and incorporated herein. The fact is that as compared with the patented variety "Greenwich", U.S. Plant Pat. No. 5,550, it produces substantially greater quantities of Asparagus. In fact as compared with the known standard "Mary Washington", an unpatented variety, "Jersey Gem" is definitely substantially better in the Oklahoma test and as a matter of fact in other tests where it has been compared with "Mary Washington" likewise.

The Michigan tests disclose that this particular Asparagus plant, is in the top ten for both locations in Michigan where the plant was grown for test purposes.

These tests have extended over a number of years and thus establish that the plant is a good producer, and the characteristics of the plant produced by us through asexual reproduction, have been found to come true in successive generations and thus establish the fixed characteristics which we have described and which are outstanding as will be understood.

In summary, the plant may be compared with others which we have produced and for that purpose reference is made to the drawing wherein the stalk data are applied to a typical plant in some areas so as to enable a comparison to be made with other varieties and in dealing with the actual production in quantities thereof, the tables supplied are also of assistance.

Figure 2:
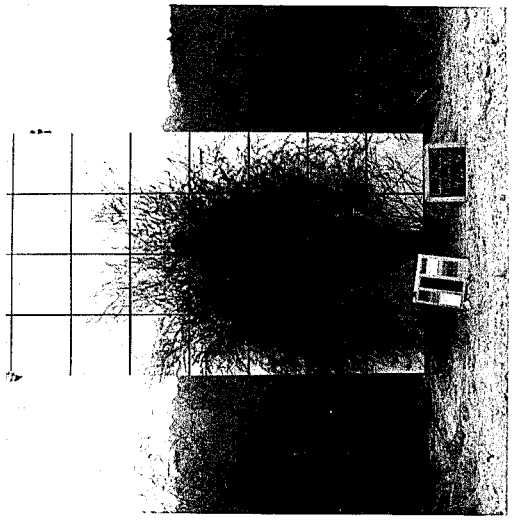
Figure 1:
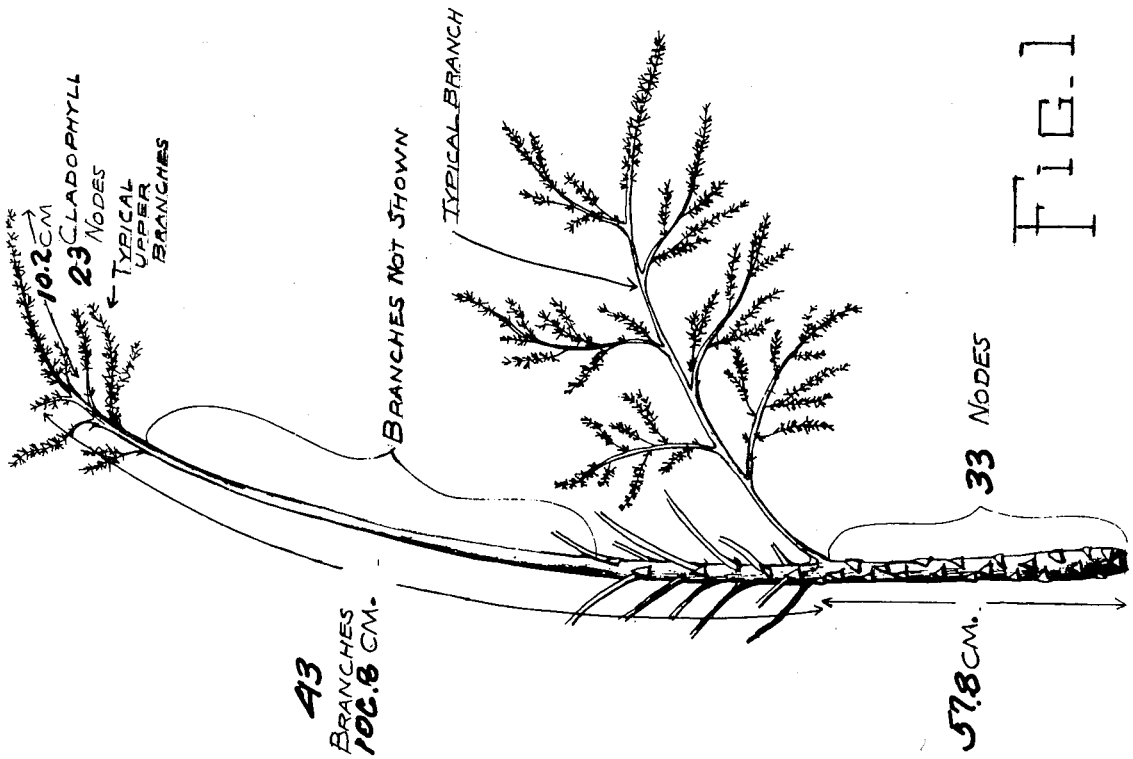
FIG. 1 is a mechanical drawing of portions of an Asparagus plant showing length of the main stem to the lowest branch and typical dimensions, of the upper branches of 'Jersey Gem'; and, FIG. 2 is a photographic depiction showing in side-view a specimen of 'Jersey Gem' in an observation plot.

It should be noted that the color picture of FIG. 2 in the drawing, is referred to the Munsell Color Cascade by way of designation of particular colors, it however being noted that as such Asparagus plants do not have the widely varying color differences which some other plants may exhibit.

In any event, the drawing herein does assist in identifying and in disclosing some of the attributes of our new Asparagus plant, as can be depicted in such illustration.

We have established by asexual reproduction effected through crown division that the characteristics set forth herein come true in successive generations.

ASPARAGUS PLANT DATA

| | Inch × 2.54 = cm. |
|---|---|
| **STALK DATA** | |
| **The dimensions to follow are presented in centimeters unless otherwise indicated. The number "(1)" indicates that the measurements were taken from the largest stalk** | |
| Number of nodes below first branch (1) | 33 |
| Number of cm. from crown to first branch (1) | 57.8 |
| Number of branches (1) | 43 |
| Number cm. between first and last branch (1) | 106.0 |
| Internode length in cm. between branches | 2.47 |
| Number of cladophyll nodes beyond last branch | 23 |
| Number of cm. beyond last branch (1) | 10.2 |
| Internode length in cm. beyond last branch (1) | 0.443 |
| Largest stalk diameter in mm | 17.9 |
| Mean diameter of three largest stalks in mm | 17.0 |
| Number of stalks | 22 |
| Stalk vigor index (No. × (Mean Diam.) | 6,358 |
| Mature stalk color, bloom removed, Color No. (1) | 21–13 |

-continued

| | |
|---|---|
| Highest headed stalk cm. to first branch | 82.6 |

FLOWER DATA

The number "(1)" below indicates that the color number identification was taken from *Munsell Limit Color Cascade*, Munsell Color.

| | |
|---|---|
| Petal tip (yellow) Color No. (1) | 26-3.5 |
| Petal base (green) Color No. (1) | 24-4 |
| Flower length mm | 5.91 |
| Flower width at midpoint mm | 2.74 |

Flowers are male, typical of the specie.

CLADOPHYLL DATA

| | |
|---|---|
| Number per node | 4.67 |
| Length mm | 16.0 |
| Width mm | 0.143 |

OKLAHOMA

| HYBRID | CUM. kg/ha |
|---|---|
| Jersey Gem | 29,422 |
| G27 × 22-8 | |
| Greenwich | 23,688 |
| 53 × 22-8 | |
| Mary Washington | 11,305 |

MICHIGAN

| | 1986 | |
|---|---|---|
| Cultiver | Lb/A | Rank |
| Jersey Giant | 5416 | 1 |
| G27 × 22-8 mm | 5325 | 2 |
| Mary Washington | 1357 | 61 |
| Jersey Giant | 3300 | 8 |
| 47 × 14-4 mm. | 3266 | 9 |
| Mary Washington | 2070 | 42 |

Note: Entries in the top ten for both locations among 51 cultivars.

ASPARAGUS YIELD DATA

| HYBRID | CUM. kg/ha |
|---|---|
| Jersey Gem (1) | 20,477 |
| G27 × 22-8 | |
| Greenwich | 15,359 |
| 53 × 22-8 | |
| Jersey Giant | 13,033 |
| 56 × 22-8 | |

(1) Ranked No. 1 in a trial of 30 cultivars (in this trial)

We claim:

1. A new and distinct Asparagus hybrid as hereinbefore shown and described, characterized particularly as to novelty by the unique combination of exceptionally high yield of good quality spears under widely diverse conditions of soil and climate, as compared with a large number of other hybrid Asparagus, its all male characteristics, and resistance to rust (*Puccinia asparagi*).

* * * * *